United States Patent
Mueller

(10) Patent No.: US 9,089,410 B1
(45) Date of Patent: Jul. 28, 2015

(54) UNDER-EYE STRIP

(75) Inventor: Brett Mueller, Middleton, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 1089 days.

(21) Appl. No.: 12/537,864

(22) Filed: Aug. 7, 2009

Related U.S. Application Data

(60) Provisional application No. 61/087,525, filed on Aug. 8, 2008, provisional application No. 61/087,655, filed on Aug. 9, 2008.

(51) Int. Cl.
*A61F 9/04* (2006.01)
*A41D 13/11* (2006.01)

(52) U.S. Cl.
CPC ...................................... *A61F 9/04* (2013.01)

(58) Field of Classification Search
CPC ........... A61F 9/045; A61F 9/04; A61F 9/029; A61F 9/026; A41D 13/11; A41D 13/1153
USPC ............... 2/1, 455, 424, 425, 15, 432, 9, 206, 2/209.13, 174; 128/858, 156; 132/88.5, 132/58.7, 319; 156/230; 351/41, 44, 51, 52; 473/422; D2/865, 866, 895; D24/189; 428/364, 370, 373
See application file for complete search history.

(56) References Cited

U.S. PATENT DOCUMENTS

| | | | | |
|---|---|---|---|---|
| 2,238,098 | A * | 4/1941 | Bradshaw | 139/391 |
| 2,842,142 | A * | 7/1958 | Peck | 132/216 |
| 3,024,518 | A * | 3/1962 | Newton | 28/159 |
| 3,823,723 | A * | 7/1974 | Miller | 132/201 |
| 4,203,435 | A * | 5/1980 | Krull et al. | 602/47 |
| 4,285,338 | A * | 8/1981 | Lemelson | 602/58 |
| 4,500,571 | A * | 2/1985 | Jones | 428/13 |
| 4,719,909 | A * | 1/1988 | Micchia et al. | 128/858 |
| 4,745,916 | A * | 5/1988 | Seber | 128/858 |
| 4,964,428 | A * | 10/1990 | Lamatrice | 132/216 |
| 5,765,231 | A * | 6/1998 | Leonard et al. | 2/206 |
| 5,939,142 | A * | 8/1999 | Comiskey et al. | 427/256 |
| 6,096,154 | A * | 8/2000 | Comiskey et al. | 156/230 |
| 6,350,338 | B1 * | 2/2002 | Comiskey et al. | 156/230 |
| 6,537,660 | B2 * | 3/2003 | Katayama et al. | 428/364 |
| RE38,246 | E * | 9/2003 | Leonard et al. | 2/206 |
| 6,632,499 | B1 * | 10/2003 | Marks et al. | 428/42.1 |
| 2001/0047847 | A1 * | 12/2001 | Kukoff | 156/279 |
| 2004/0031085 | A1 * | 2/2004 | Widdemer | 2/161.2 |
| 2006/0231188 | A1 * | 10/2006 | Wen | 156/72 |
| 2009/0229742 | A1 * | 9/2009 | Livacich et al. | 156/247 |

FOREIGN PATENT DOCUMENTS

EP      354884 A2 *  2/1990

* cited by examiner

*Primary Examiner* — Gloria Hale

(74) *Attorney, Agent, or Firm* — Rick L. Abegglen

(57) ABSTRACT

An improved under-eye strip that reduces low-angle reflected light compared to the prior art through the use of a fuzzy material on the exposed surface of the strip.

14 Claims, 13 Drawing Sheets

LIGHT RAYS SHINING ON
A FUZZY SURFACE

UNDER-EYE STRIP

CROSS-REFERENCE TO RELATED APPLICATIONS

This application claims priority to provisional application No. 61/087,655 filed Aug. 9, 2008, the disclosure of which is incorporated by reference. This application claims priority to provisional application No. 61/087,525 filed Aug. 8, 2008, the disclosure of which is incorporated by reference.

FIELD OF THE INVENTION

This invention relates generally to the field of sporting goods and athletic competition. More particularly, the present invention relates to an improved under-eye strip that reduces low-angle reflected light compared to the prior art.

BACKGROUND OF THE INVENTION

Athletes have applied various forms of eye black under their eyes for many years. According to the Dec. 3, 2006 New York Times, eye black was used in professional football at least as early as 1942. Athletes use eye black for various reasons, for example because they believe it reduces glare off their cheeks and will thereby improve their ability to catch or hit a ball, or because they believe it creates an intimidating appearance. No matter what the reason, it is clear that athletes from grade school up to professional levels like to wear eye black in its various forms.

The first eye black products were most likely grease paint or burnt cork. Grease paint products are still used for this purpose, including stick products for convenient application. U.S. Pat. No. 4,719,909 teaches an under eye light absorbing device in the form of adhesive patches that avoids some of the problems with grease paint, for example ease of application and removal.

What is needed is an improved glare reducing strip that reduces the light that is likely to enter the eye due to reflection from the strip when worn.

SUMMARY OF THE INVENTION

A first embodiment of the invention is an under-eye strip having a fuzzy surface.

A second embodiment of the invention is a method of using an under-eye strip having a fuzzy surface.

A third embodiment of the invention is a method of manufacturing an under-eye strip having a fuzzy surface.

Further objects, features, and advantages of the invention will be apparent from the following detailed description when taken in conjunction with the accompanying drawings.

DETAILED DESCRIPTION OF THE INVENTION

Figure 1:
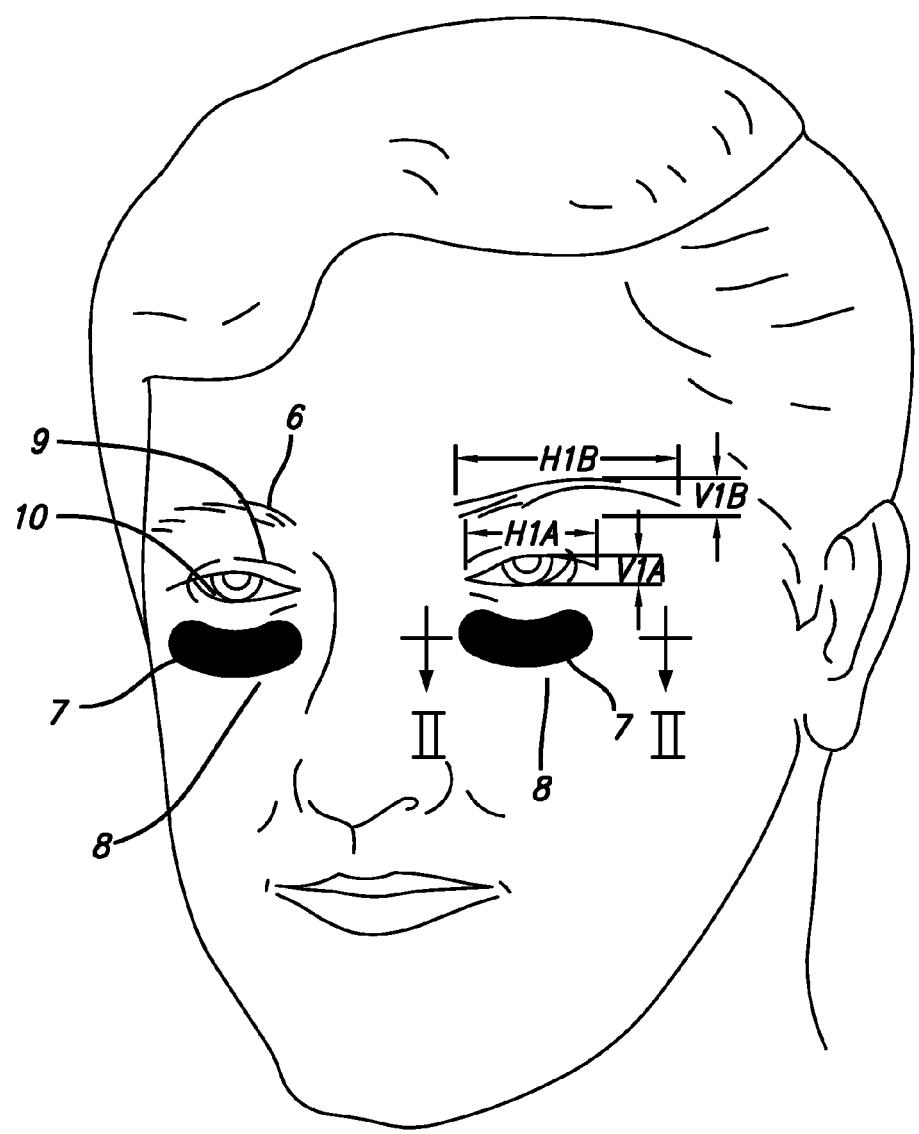
FIG. 1 depicts a pair of under-eye strips worn by a person.

FIG. 1 depicts a pair of under-eye strips 7 applied to the areas 8 located below the eyebrows 6, eye sockets 9 and eyes 10 of a person, as is known in the prior art, for example in U.S. Pat. No. 4,719,909. The eyes 10 have a vertical dimension VIA and a horizontal dimension H1A. The eyebrows 6 have a vertical dimension V1B and a horizontal dimension H1B.

Figure 2:
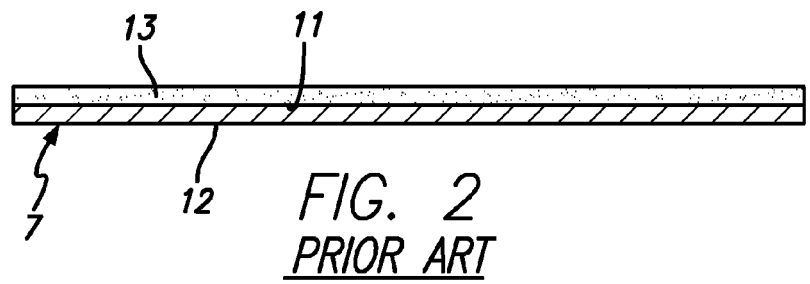
FIG. 2 is a cross section of an under-eye strip of FIG. 1 taken along the line II-II.

FIG. 2 is a cross section of an under-eye strip 7 of FIG. 1 taken along the line II-II. The under-eye strip 7 can comprise a body 11 that includes an exposed surface 13 and a pressure sensitive adhesive layer 12, as is known in the prior art.

Figure 3:
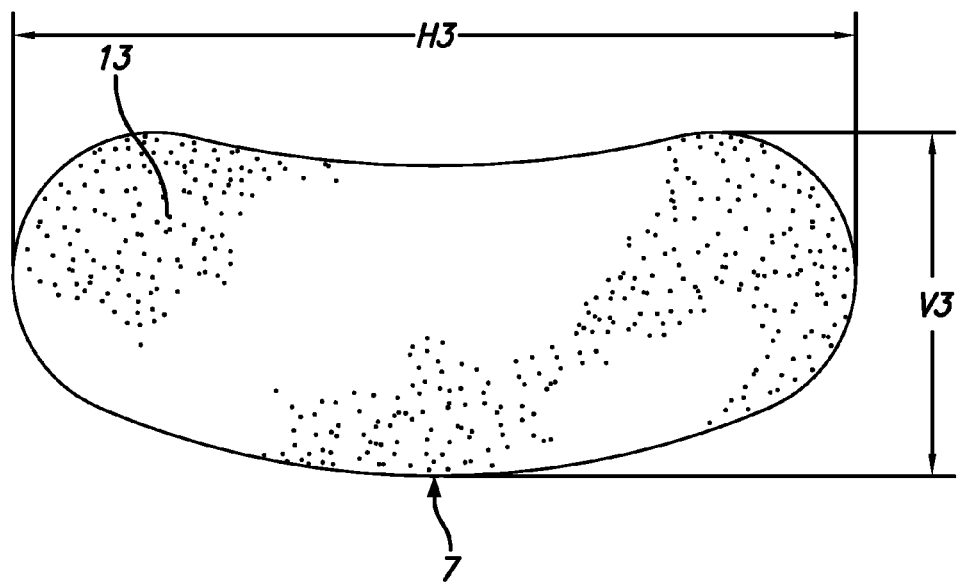
FIG. 3 is a plan view of a typical under-eye strip.

FIG. 3 is a plan view of a typical under-eye strip, as is known in the prior art, showing the exposed surface 13 when the under-eye strip is laid flat on a plane. The under-eye strip 7 has a horizontal dimension H3 and a vertical dimension V3. As shown in FIG. 3, the vertical dimension of the under-eye strip is about half the horizontal dimension. The dimensions H3 and V3 of the under-eye strip 7 make it large enough to be plainly visible to the naked eye without magnification. By comparison to the dimensions of the human eye and face, as shown in FIG. 1, the order-of-magnitude of H3 and V3 is about one inch.

Figure 4:
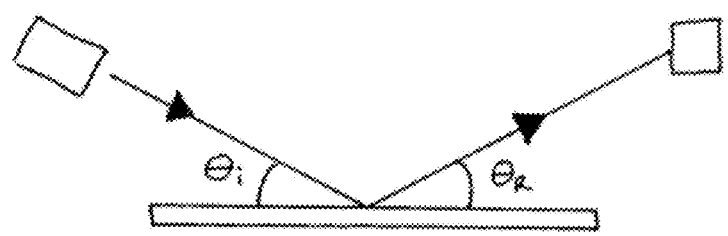
FIG. 4 is a diagram of light reflecting from a planar surface.

FIG. 4 is a diagram of light reflecting from a planar surface (such as a mirror), showing that the angle of incidence $\Theta i$ is equal to the angle of reflectance $\Theta r$.

Figure 5:
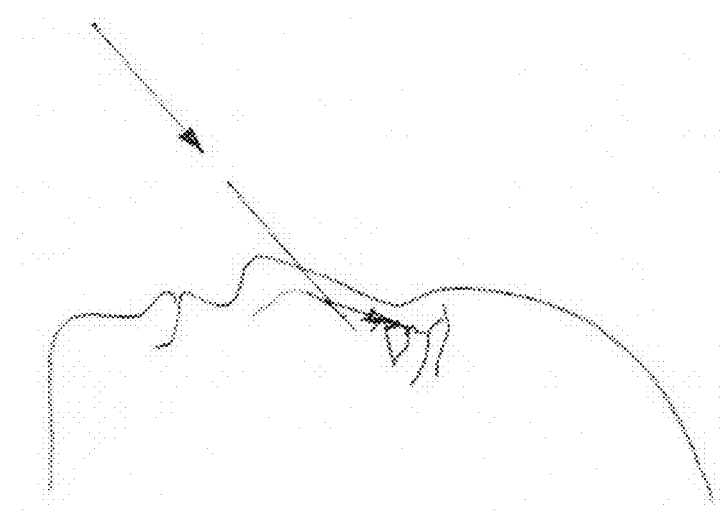
FIG. 5 is a diagram showing how light could reflect from the portion of a person's face where an under-eye strip would be worn.

FIG. 5 is a diagram showing how light could reflect from the portion of a person's face where an under-eye strip would be worn. Although the face of a person is not planar, the eye sockets are located close to the same plane as the area 8 below the eye sockets 9. For this reason, any light reflecting from the area 8 could only enter the eye 10 if it reflects at a relatively low angle, for example at about 30 degrees or less from the horizontal. Even this low angle light would be most likely to enter the periphery of the eye, rather than the center of the pupil, because that periphery tends to be farther from the plane of the area 8. Because the angle of reflection is equal to the angle of incidence, this means that reflectivity of low angle light is most important in terms of reducing light that enters the eye after reflecting from the area 8.

Figure 6:
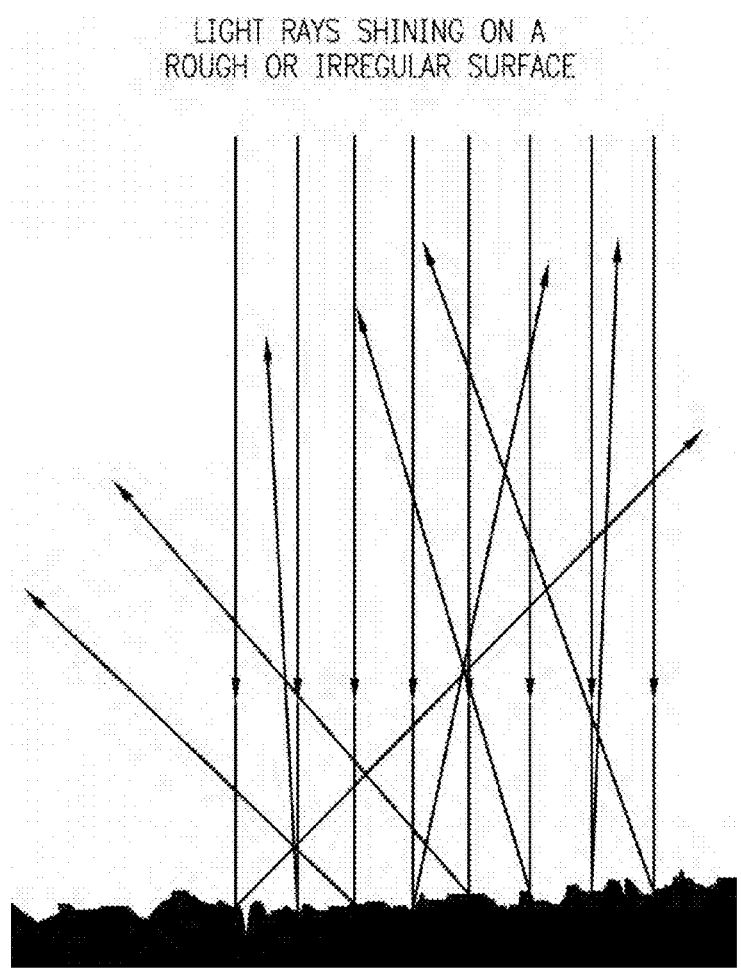
FIG. 6 is a diagram of light reflecting from an irregular surface.

FIG. 6 is a diagram of light reflecting from an irregular surface, showing that this kind of surface tends to scatter and disperse reflected light.

Figure 7A:
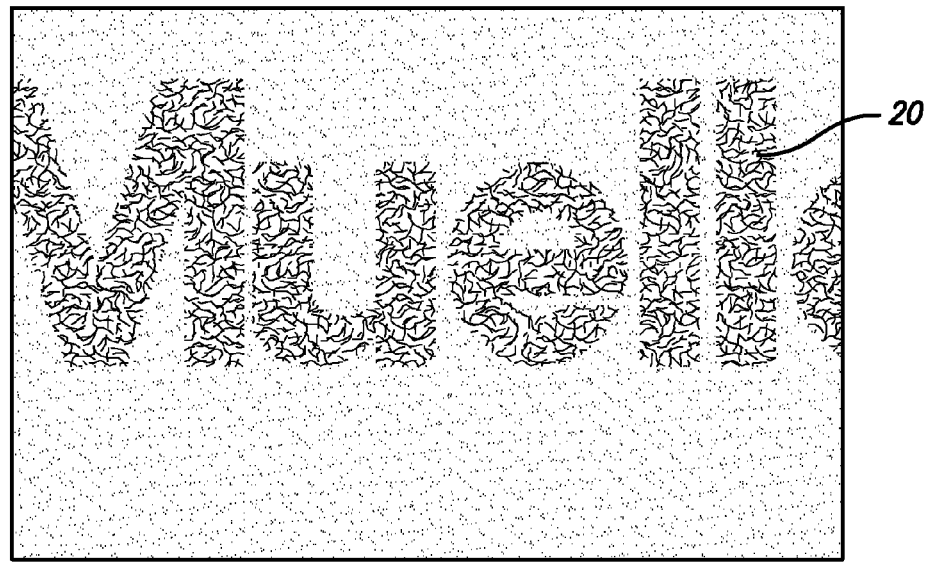
FIGS. 7(a) and 7(b) are microscope photographs at different magnifications of the surface of a first exemplary prior art under-eye strip.
Figure 7B:
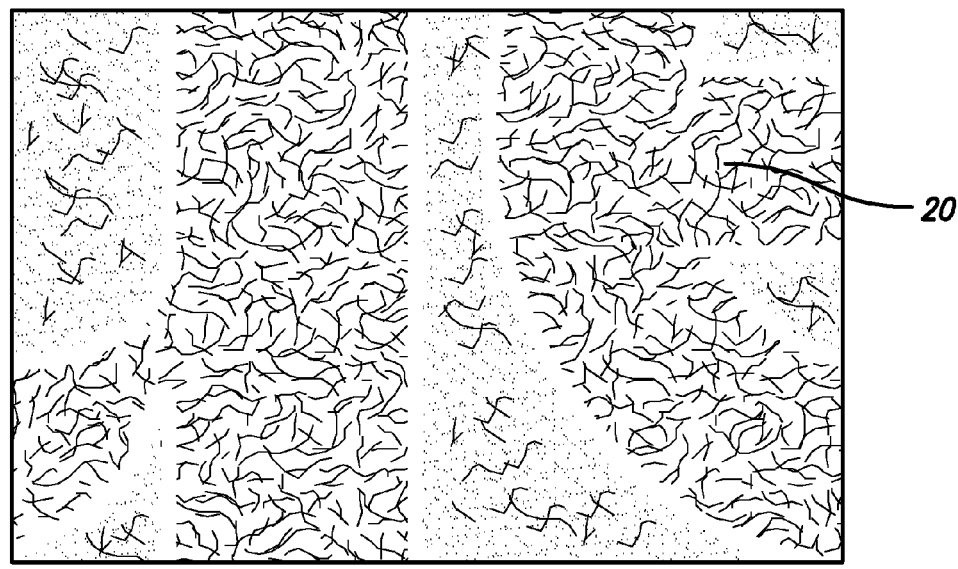

FIGS. 7(a) and 7(b) are microscope photographs at different magnifications of the surface of a first exemplary prior art under-eye strip 20. This prior art under-eye strip 20 has a relatively smooth surface. Although fibrous, the strip 20 has a relatively planar surface since the fibers are mashed down and immobile. The logo on the strip 20 is printed on top of the fibers.

Figure 8A:
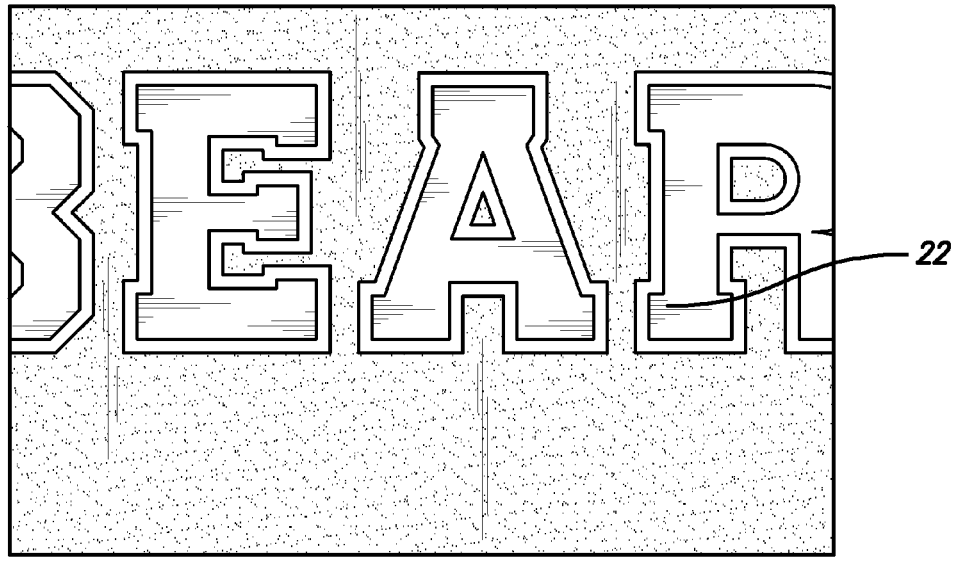
FIGS. 8(a) and 8(b) are microscope photographs at different magnifications of the surface of a second exemplary prior art under-eye strip.
Figure 8B:
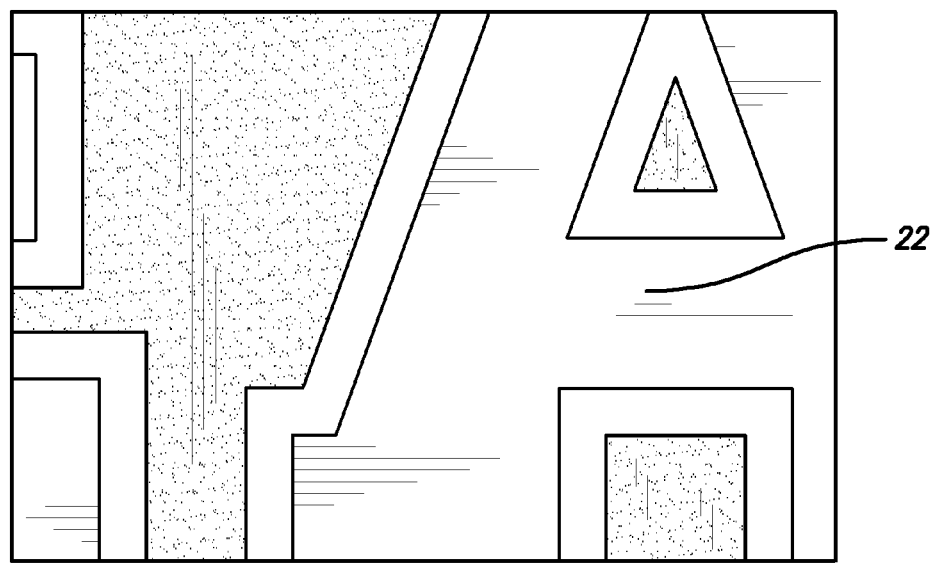

FIGS. 8(a) and 8(b) are microscope photographs at different magnifications of the surface of a second exemplary prior art under-eye strip 22. This prior art under-eye strip 22 also has a relatively smooth surface with some surface crinkling. The exact manufacturing process and construction of the strip 22 is not known. However, the strip 22 is believed to be made as a conventional decal with a logo applied to the decal using an inkjet printer or similar technology.

Figure 9A:
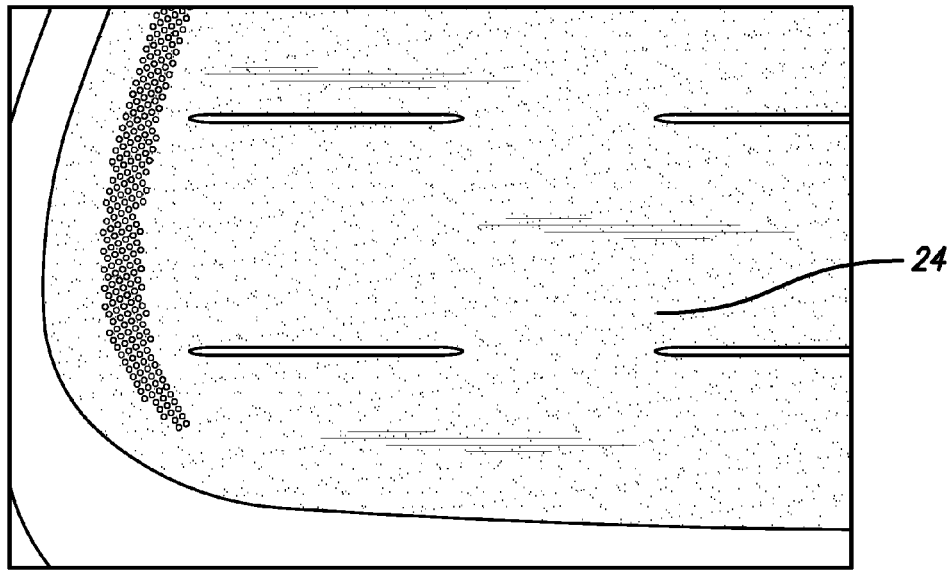
FIGS. 9(a) and 9(b) are microscope photographs at different magnifications of the surface of a second exemplary prior art under-eye strip.
Figure 9B:
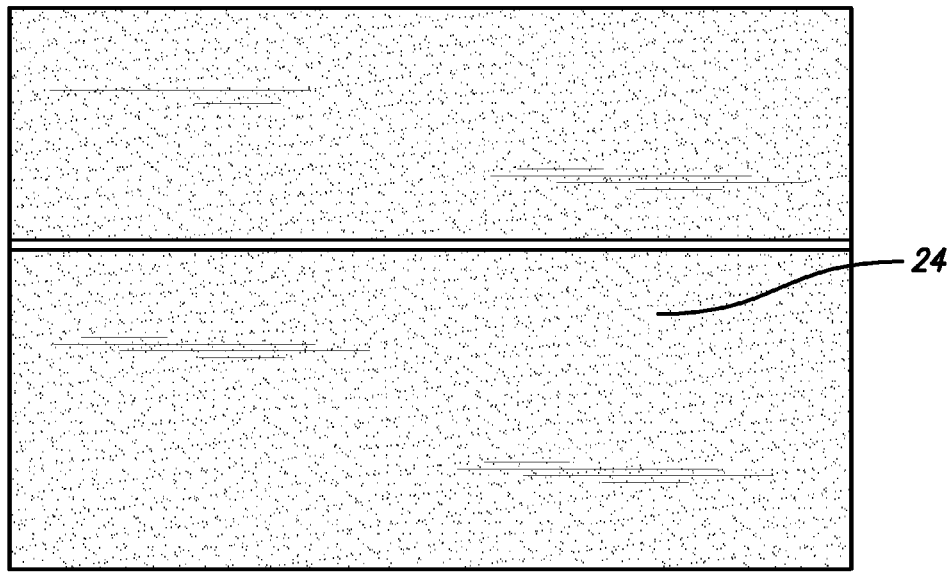

FIGS. 9(a) and 9(b) are microscope photographs at different magnifications of the surface of a second exemplary prior art under-eye strip 24. This prior art under-eye strip 24 also has a relatively smooth surface with some surface crinkling. The under-eye strip 24 is believed to be essentially identical to the under-eye strip 22 except without any logo.

Figure 10A:
FIGS. 10(a) and 10(b) are microscope photographs at different magnifications of the surface of an exemplary under-eye strip according to the present invention.
Figure 10B:

FIGS. 10(a) and 10(b) are microscope photographs at different magnifications of the surface of an exemplary under-eye strip 30 according to the present invention. The under-eye strip 30 is formed of artificial suede, and differs from the exemplary prior art strips 20, 22, and 24 because the surface of the strip 30 is not relatively smooth and planar. In contrast, as perhaps best shown in FIG. 10(b) the surface of the strip 30 is very irregular and fuzzy, many air-filled voids appear between the fibers that make up that surface, and portions of the fibers themselves are relatively free to move and unfixed. The microscope photographs of FIGS. 10(a)-10(b) show microscopic fibers that are too short to be plainly visible as individual fibers to the naked eye. In contrast, the dimensions H3 and V3 (of the under-eye strip 7) are large enough that the under-eye strip 7 is plainly visible to the naked eye, as shown in FIGS. 1-3.

The under-eye strip 30 can be made by rolling a suitable sheet material together with a release paper coated with one or more suitable pressure sensitive adhesives. The under-eye strip 30 of FIGS. 10(a)-10(b) uses as a sheet material a synthetic or artificial suede material known as RIMA 0854 sold by Daewoo International of Kangseo-gu Busan, Korea, although other materials can be used in an under-eye strip 30 according to the invention. The initial color of the sheet material used in the under-eye strip 30 is white, although this is not required. The under-eye strip 30 of FIGS. 10(a)-10(b) uses a release paper coated with adhesive known as TM9730 sold by MacTac of Stow, Ohio, although this is not required.

After rolling the suitable sheet material together onto the release paper coated with adhesive, the exposed surface of the sheet material can be coated or imprinted with a suitable ink or dye. The under-eye strip 30 of FIGS. 10(a)-10(b) uses a water-based non-toxic ink known as NO-TOX™ NT23BR sold by Color Con of Chalfont, Pa., although this is not required. In the under-eye strip 30, most of the surface of the strip 30 is printed black, but the central portion is left unprinted to leave white areas in the form of the manufacturers trademark. However, this is not necessary and the entire surface of the strip could be printed black.

After printing onto the exposed surface of the sheet material, the sheet material can be die-cut (without cutting the release paper) into multiple strips 30 having the desired shape. Although the under-eye strip 30 is preferably cut into the kidney shape shown in FIG. 3, this is not required and other shapes can be used. After the strips 30 are die cut, the release paper can be cut into convenient sizes for packaging and sale. For example, a single sheet of release paper could carry 4-6 under eye strips 30.

Figure 11:
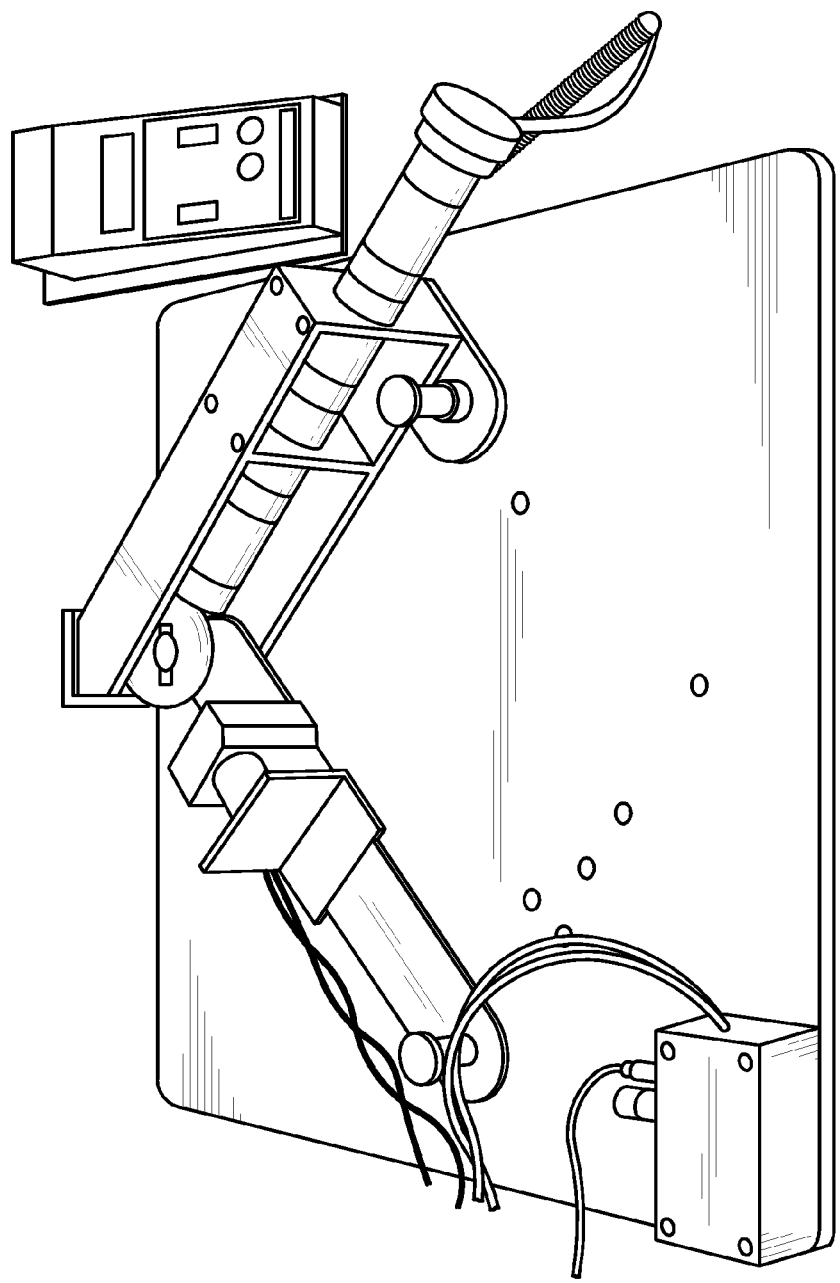
FIG. 11 is a picture of a test apparatus used to measure the amount of light that reflects from under-eye strips at specific angles of incidence and reflection.

FIG. 11 is a picture of a test apparatus used to measure the amount of light that reflects from under-eye strips at specific angles of incidence and reflection. A light source mounted to a movable arm appears on the left side of the apparatus, with one end of the movable arm attached to a hinge in the upper center of the apparatus. A photoreceptor able to measure light intensity is mounted to another movable arm on the right side of the apparatus, with one end of that movable arm also attached to the hinge in the upper center of the apparatus. A sample holder is mounted at the hinge in the upper center of the apparatus, between the two arms.

This apparatus allows the measurement of light reflected from samples mounted on the sample holder, with the light source and photoreceptor able to be positioned at various (and equal) angles relative to the surface of the sample and sample holder. For example, the apparatus allows measurement of light reflected from the sample at low angles (approximately 30 degrees) of incidence and reflection. The apparatus also allows rotation of the sample in the sample holder, so that reflectance can be measured at different rotational positions of the sample relative to the plane of the light source and photoreceptor arms.

The apparatus of FIG. 11 was used to measure the amount of light that reflects from the under-eye strips 20, 22, 24, and 30 at low angles (approximately 30 degrees) of incidence and reflection, and at multiple rotational positions. Three samples of each of the under-eye strips 20, 22, 24, and 30 were each attached to a separate 1"×2" piece of flat black picture mounting board. Three "control" samples of white paper are also prepared for the purpose of comparison.

After mounting the samples to mounting boards, the light source and photoreceptor arms were positioned at approximately 60 degrees from the plane of the sample holder. The sample holder was set to a first rotational position, and a white "control" sample was inserted into the sample holder. The intensity of the light source was adjusted to obtain a standardized reading of about 6500 LUX. The sample holder was set to additional rotational orientations, and light intensity was measured at each of these rotational positions. The procedure was repeated with all three white "control" samples to verify the repeatability and consistency of the measurements.

After setting up the test apparatus using the white "control samples", the low angle light reflected from a sample of each of the under-eye strips 20, 22, 24, and 30 was measured at two rotational positions in the sample holder, with the light source and photoreceptor arms fixed at approximately 30 degrees from the plane of the sample holder. Besides the under-eye strips 20, 22, 24, 30, and the white paper control, an additional blank under-eye strip according to the invention (the "blank strip") was tested, where the blank strip has identical construction to strip 30 except that the entire surface of the blank strip is printed black so that it does not contain any manufacturer's logo. The averaged results are presented in Table 1 and shown in FIG. 12. The values in the table are in Lux.

TABLE 1

| Strip 22 (with logo) | Strip 24 (no logo) | White Paper | Strip 20 (with logo) | Strip 30 (with logo) | blank strip (no logo) |
|---|---|---|---|---|---|
| 12545 | 8665 | 6130 | 2830 | 1840 | 563.5 |

Figure 12:
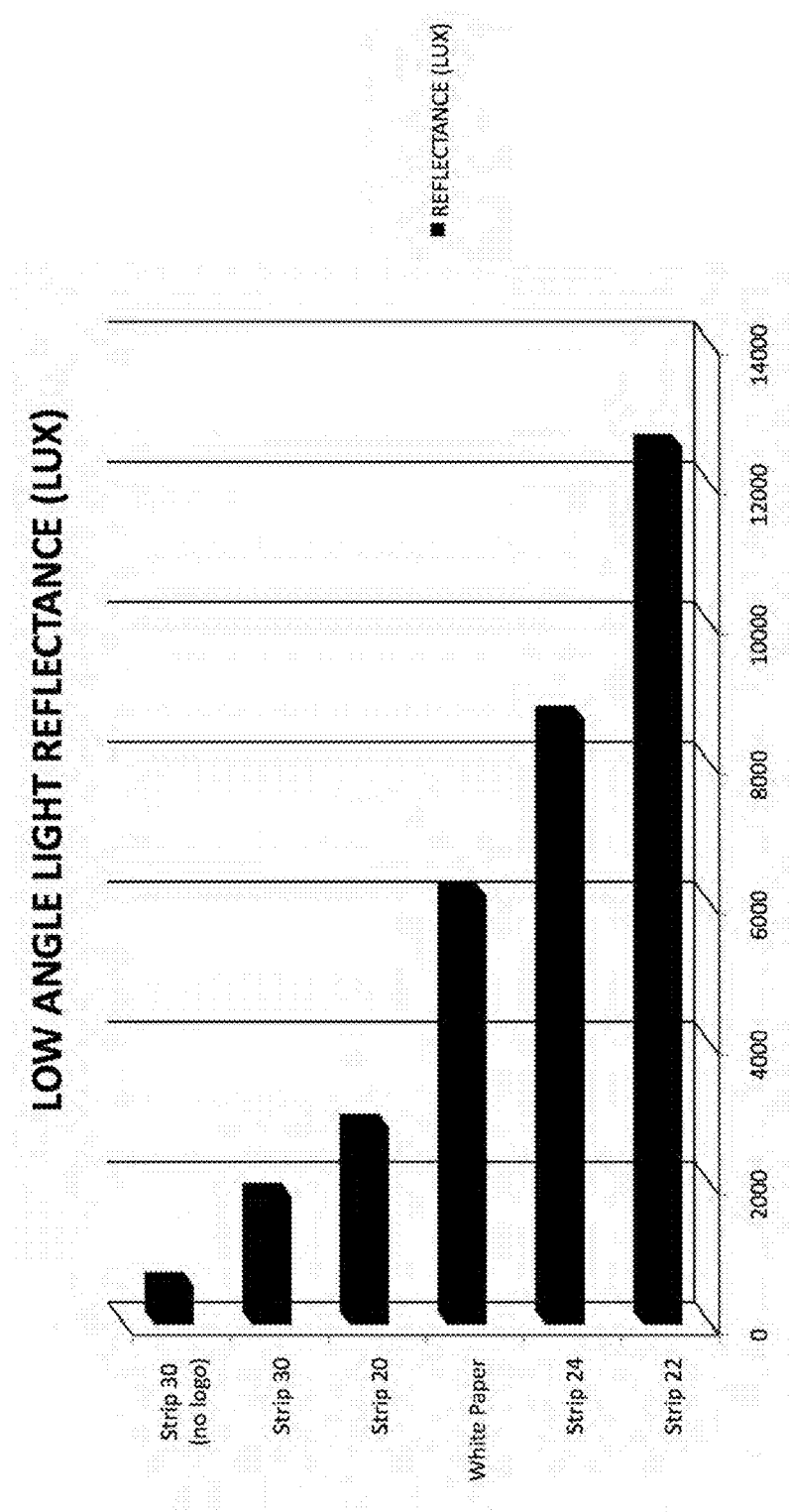
FIG. 12 is a graph of the relative amount of low-angle light reflecting from the under-eye strips of FIGS. 7-10.

FIG. 12 presents the values in Table 1 in the form of a graph showing the relative amount of light reflecting from the under-eye strips 20, 22, 24, and 30 of FIGS. 7-10, as well as from white paper control samples and the blank strip discussed above. As can be seen from Table 1, among strips having a common construction (e.g. strips 22 & 24 or strips 30 and the blank strip), a strip bearing a logo generally reflects more than a strip that does not bear a logo. So the most appropriate apples-to-apples comparison of the performance due to construction would compare strip 22 to strip 30 (for strips with logos) and compare strip 24 to the blank strip (for strips without logos).

As can be seen from Table 1 and FIG. 12, the strips 30 and the blank strip have dramatic and unexpectedly superior performance compared to prior art strips. Compared to strip 22, strip 30 reflects only 1840/12545=14.7% as much low angle light. Compared to strip 24, the blank strip reflects only 563.5/8665=6.5% as much low angle light.

Figure 13A:
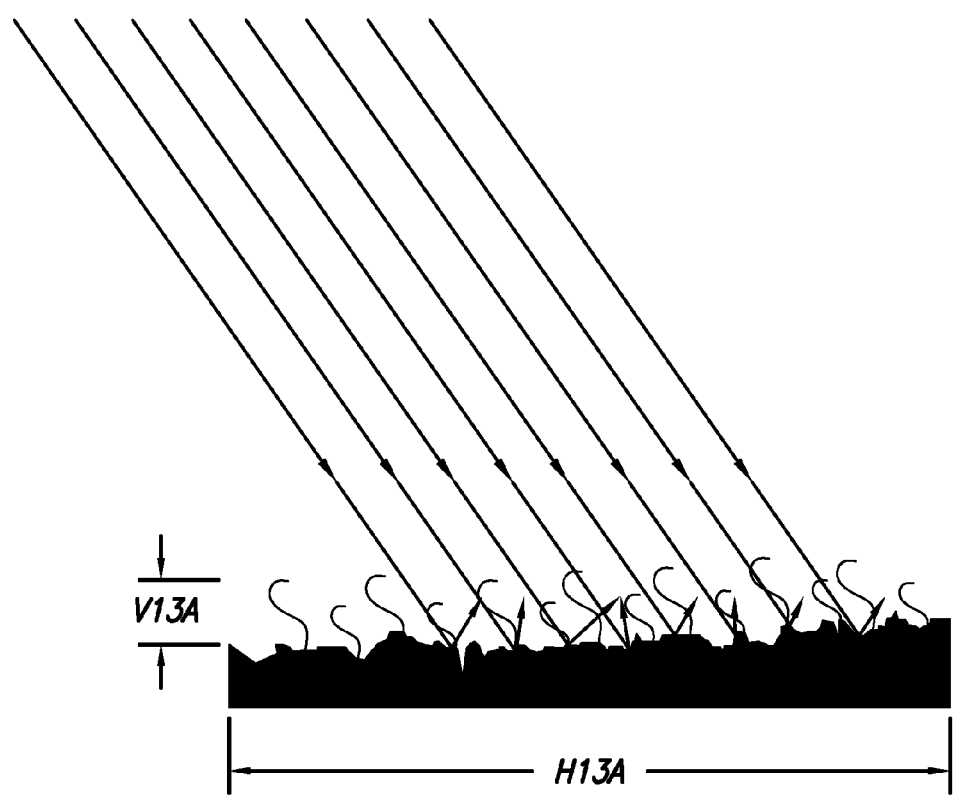
FIGS. 13(a), 13(b), and 13(c) are diagrams of light shining onto fuzzy, loop, and cut-loop surfaces, respectively.
Figure 13B:
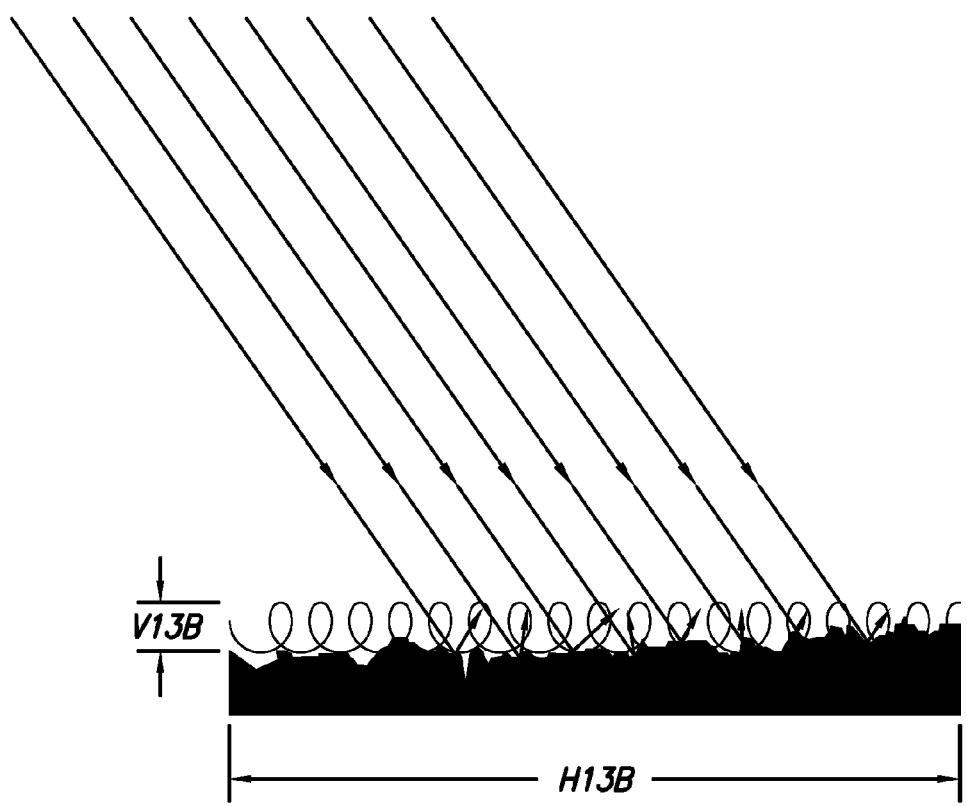
Figure 13C:
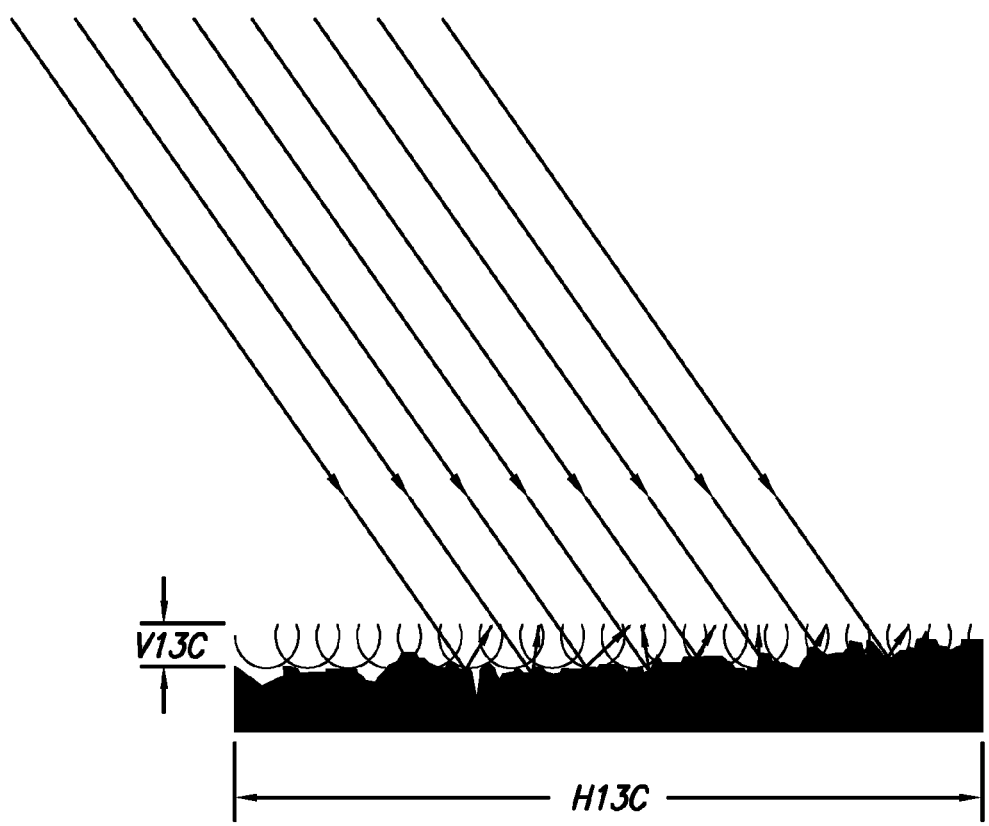

FIGS. 13(*a*), 13(*b*), and 13(*c*) are microscopic diagrams of light shining at a relatively low angle onto three types of fuzzy surfaces: randomly fuzzy, loop, and cut-loop surfaces respectively. These figures are meant to help explain why fuzzy materials reduce low-angle reflected light more than generally planar surfaces, as an explanation only and not as a limitation on the scope of the claims. In FIG. 13(*a*), the microscopic fibers have a vertical dimension V13A and the surface has a horizontal dimension H13A. In FIG. 13(*b*), the microscopic fibers have a vertical dimension V13B and the surface has a horizontal dimension H13B. In FIG. 13(*c*), the microscopic fibers have a vertical dimension V13C and the surface has a horizontal dimension H13C. As shown in these figures, as well as in FIGS. 10(*a*)-10(*b*), all three types of surfaces are formed of microscopic (not plainly visible as individual fibers to the naked eye) fibers, that extend outwardly in multiple directions from the material surface to thereby form the fuzzy surface of the materials.

Generally, it is believed that incoming light penetrates the fuzzy material to a point of reflection that lies between the top of the fuzz and the bottom of the fuzz. At the point of reflection, the incoming light is partially absorbed and partially reflected as attenuated reflected light. The degree of absorption depends on the material, which can be chosen to absorb as much light as possible (e.g dull black materials instead of white or reflective materials).

The attenuated reflected light will also be scattered to a degree that depends on the material. The material can be chosen to scatter the light as much as possible (e.g. rough and irregular materials instead of smooth planar materials).

Because the point of reflection is within the fuzz in materials such as those shown in FIGS. 10(*a*)-10(*b*) and 13(*a*)-13(*c*), the attenuated and scattered reflected light is still within the fuzzy material as it departs the point of reflection. This reflected light will typically not have a clear path out of the fuzz, and it may very well strike the fuzz fibers one or more additional times on its way out. These multiple reflections/absorptions will attenuate and scatter the reflected light even more, with the end result being that only a small portion of the incoming light eventually exits the fuzz. It is believed that fuzzy materials with superior performance in trapping reflected light will have fuzz with adequate space (air) between the fibers so that the fuzz is not too dense (so the incoming light can penetrate at least part of the way into the fuzz) and not too thin (so any reflected light will be likely to run into the fuzz again on its way out).

It is believed that this "trapping" of the reflected light does not occur in the prior art strips because the surfaces of those prior art strips are relatively planar. Once the light reflects the first time off the surface of prior art strips, there is no opportunity for the reflected light to be absorbed or scattered again through subsequent reflections/absorptions as can occur with the fuzzy materials.

While the preceding discussion of the exemplary glare reducing strip 30 identifies a particular artificial suede material as a suitable sheet material, this is not required and other textured or fuzzy materials could be used. A flocked material having a dull irregular surface could also be used, for example of the types available from Fiberlok, Inc. of Fort Collins, Colo. or from Microfibres, Inc. of Pawtucket, R.I. A felt product having a dull irregular surface could also be used, for example of the types available from Aetna Felt Corporation of Allentown, Pa. or 3M Corporation of St. Paul, Minn.

While the preceding discussion of the exemplary glare reducing strip 30 refers to the particular kidney shape shown in FIG. 3, this is not required and other shapes could be used. The term "under-eye strip" as used herein is intended to encompass strips made with both adhesive patch construction and also with decal construction.

It is understood that the invention is not confined to the embodiments set forth herein as illustrative, but embraces all such forms thereof that come within the scope of the following claims.

What is claimed is:

1. An anti-glare under-eye strip comprising a material sheet shaped and sized for placement on a skin area located under a wearer's eye on the upper edge of said wearer's cheek;

said material sheet having an outwardly facing surface and an inwardly facing surface with adhesive thereon to thereby attach said inwardly facing surface of said material sheet to said skin area;

said outwardly facing exposed surface including longitudinally outwardly extending fibers extending outwardly from said exposed surface in multiple directions, said fibers are too short to be plainly visible as individual fibers to a viewer's naked eye and are only visible when viewed with a microscope whereby said longitudinally extending fibers on said outwardly facing surface forms a fuzzy appearance on said surface when viewed through said microscope; and wherein said fuzzy surface interferes with the glare-causing light that hits the anti-glare under-eye strip on said wearer's cheek when worn so that said wearer's vision is not interfered with by said glare causing light and reflection froim said cheek skin surface.

2. The under-eye strip of claim 1 wherein the exposed surface includes an artificial suede material.

3. An anti-glare under-eye strip comprising a material sheet shaped with a horizontal dimension and a vertical dimension of a size for placement on a skin area located under a wearer's eye on the upper edge of said wearer's cheek;

said material sheet having an outwardly facing surface and an inwardly facing surface with adhesive thereon to thereby attach said inwardly facing surface of said material sheet to said skin area;

said outwardly facing exposed surface including longitudinally outwardly extending fibers extending outwardly from said exposed surface in multiple directions, said fibers are too short to be plainly visible as individual fibers to a viewer's naked eye and are only visible when viewed with a microscope whereby said longitudinally extending fibers on said outwardly facing surface forms a fuzzy appearance on said surface when viewed through said microscope; and wherein said fuzzy surface interferes with the glare-causing light that hits the anti-glare under-eye strip on said wearer's cheek when worn so that said wearer's vision is not interfered with by said glare causing light and reflection from said cheek skin surface.

4. The under-eye strip of claim 3 wherein the exposed surface includes an artificial suede material.

5. The under-eye strip of claim 1 wherein the exposed surface includes markings that communicate information.

6. The under-eye strip of claim 5 wherein the markings comprise portions of the exposed surface imprinted with ink or dye.

7. The under-eye strip of claim 1 wherein at least half of the fibers have a random orientation.

8. The under-eye strip of claim 1 wherein at least half of the fibers are formed as loops.

9. The under-eye strip of claim 1 wherein at least half of the fibers are formed as cut loops.

10. The under-eye strip of claim 3 wherein the exposed surface includes markings that communicate information.

11. The under-eye strip of claim 10 wherein the markings comprise portions of the exposed surface imprinted with ink or dye.

12. The under-eye strip of claim 3 wherein at least half of the fibers have a random orientation.

13. The under-eye strip of claim 3 wherein at least half of the fibers are formed as loops.

14. The under-eye strip of claim 3 wherein at least half of the fibers are formed as cut loops.

* * * * *